United States Patent [19]

McRae

[11] Patent Number: Plant 5,993

[45] Date of Patent: May 19, 1987

[54] ASIATIC LILY PLANT NAMED MULTNOMAH

[75] Inventor: Edward A. McRae, Boring, Oreg.

[73] Assignee: Melridge Inc., Gresham, Oreg.

[21] Appl. No.: 772,121

[22] Filed: Sep. 3, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new variety of hybrid lily plant particularly characterized by having large clusters of flowers distinguished by their rich orange-red color tone and a virtual lack of spotting, characteristics which are new in the upright Asiatic divisions of lilies suited to forcing and to mass commercial cultivation. The flowers of this plant are of excellent form, strong color, and long persistence both on the plant and as cut flowers.

The plant is highly resistant to disease and shows high tolerance of virus, it is an excellent garden plant, it is very vigorous, is a good grower and propagator, and the bulbs may be precooled and forced for cut flower production.

1 Drawing Figure

BACKGROUND OF THE NEW PLANT

This new variety of lily plant originated as a seedling selected from a group of seedlings resulting from my crossing of the clonal cultivar "Sunstar" (unpatented) and the clonal cultivar "Connecticut King" (unpatented) in the course of my breeding efforts carried on since 1975 with the object of producing spotless upright Asiatic lilies in the shades of orange and orange-red and well suited to forcing for out-of-season cut flower production, a combination of features heretofore unknown in the lily breeding art.

This new variety of lily plant has been asexually reproduced by me and under my direction at Sandy, Oreg., and successive generations produced by bulb scale propagation and natural propagation from bulblets have demonstrated that the novel and distinctive characteristics of this new variety are fixed and hold true under asexual propagation from generation to generation.

As demonstrated by successive generations of asexual propagations of this new lily plant, the clone possesses to a high degree the desirable characteristics of hybrid vigor, great hardiness, and disease resistance, as observed in western Oregon. The flowers are produced as a raceme on a single stalk, having an upright orientation, and maintain the desired characteristics of excellence of form, color and habit. The suitability of the new plant for out-of-season forcing is demonstrated by the fact that October-dug bulbs, properly precooled and potted in January, will flower under glass, in western Oregon, with no supplementary lighting and moderate greenhouse temperatures in an average of eighty to eighty-five days.

DESCRIPTION OF THE DRAWING

My new variety of lily plant is illustrated by the accompanying photographic drawing which shows buds and foliage with a group of flowers in full bloom which illustrate the flower form and tepal arrangement, one of the blossoms having been hand-painted to show the true colors of the distinctive orange-red character of the blossoms as herein specified.

DESCRIPTION OF MY NEW VARIETY

The following is a detailed description of my new variety of Asiatic lily plant as observed in greenhouse at Sandy, Oreg., with nomenclature according to The International Lily Register, Second Edition, of The Royal Horticultural Society of London, England, the color designations being according to The R.H.S. Colour Chart published by The Royal Horticultural Society in 1966.

THE PLANT

Origin: Seedling.

Parentage:

*Seed parent.*—Lilium "Sunstar" (unpatented).

*Pollen parent.*—Lilium "Connecticut King" (unpatented).

Classification:

*Horticultural.*—Division I-A, Upright Asiatic hybrid lily, according to the Horticultural Classification of Lilies, by The Royal Horticultural Society of London, England.

*Commercial.*—Hybrid Asiatic lily.

Form: An erect and stately single stem.

Height: About 90 to 100 cm. from a bulb about 15 to 18 cm. in circumference and with adequate light levels.

Growth habit: Vigorous and upright.

Foliage:

*Quantity.*—Abundant.

*Leaf size.*—About 8 to 12 cm. long and about 1 cm. wide.

*Leaf shape.*—Lanceolate.

*Texture.*—Leathery.

*Aspect.*—Glossy.

*Color.*—Both upper and lower sides, medium green, but somewhat lighter on the lower side.

Bulb size: Various, ranging to 25 cm. in circumference as used commercially.

Color: White.

THE BUD

Form: Long and obtuse ovoid.

Size: About 8 to 9 cm. long and about 5 to 6 cm. in circumference just prior to opening.

Opening rate: The bud opens slowly in response to light; this takes about one hour.

Color: Orange-red, RHS 30-C/D just prior to opening and as the tepals begin to unfurl.

Peduncle:

*Length.*—About 6 to 8 cm.

*Character.*—Erect.

*Color.*—Medium green with light plum overlay.

THE FLOWER

Blooming habit: Annually, once and profusely, in mid-season.

Size of bloom: Large, about 15 to 18 cm. in diameter; outer tepals are about 2 to 2.5 cm. wide. and the inner tepals are about 3 cm. wide Borne: As a raceme with about 8 to 10 blossoms on a single stem, from a bulb about 18 cm. in circumference.

Shape: Flattened cup-shape. The tepal tips recurve about 270°; tepal margins are lightly fluted.

Tepalage: Typical of the genus Lilium.

*Number.*—Six.

*Arrangement.*—Imbricated.

*Color.*—Orange-red, RHS 30-B/C, with a slightly deeper tone, 30-A, inbetween and adjacent to the nectaries. The nectaries are covered with very short white pubescence.

*Spotting.*—About 5 to 6 very tiny, pigmented papillae appear on the flower, parallel to the nectaries in the center of the flower.

*Color changes.*—No noticeable change in color as the flower ages.

*Tepal longevity.*—The tepals stay on the stem for about three weeks.

Appearance: The flower is shiny.

Fragrance: None.

Disease resistance: The flower and plant are resistant to Fusarium bulb rot and to Botrytis blight as observed in northern Oregon.

Lasting quality: The flower is long lasting, both on the plant and as a cut flower.

THE REPRODUCTIVE ORGANS

Stamens:

*Number.*—Six.

*Arrangement.*—Typical of genus Lilium.

Pollen and anthers (dehisced): Grayed Orange, RHS 170-A.

Filaments:

*Length.*—About 5 cm.

*Color.*—Light orange-red, RHS 30-C.

Pistils:

*Number.*—One.

*Length.*—About 5 cm.

Stigma: Soft orange-red, RHS 30-C/D.

Characteristics of ovary: Typical of genus Lilium.

THE FRUIT

Fertility: The fruit is fertile.

Shape: Ovoid.

Color at maturity: Soft brown, sometimes overlaid with soft plum.

This new variety of Asiatic hybrid lily most nearly resembles the variety 'Matchless' (U.S. Plant Pat. No. 4,879), but the new plant has larger flowers with broader and more recurved tepals, thicker tepals, and lightly ruffled tepal margins. Also, the flower color is more mellow than that of "Matchless".

I claim:

1. The new and distinctive variety of Asiatic hybrid lily plant, substantially as herein shown and described, characterized in particular by its large size and its virtually unspotted rich orange-red color, by its vigorous growth and rapid natural propagation; and by its versatility both as a garden plant and as a cut flower producer from precooled bulbs.

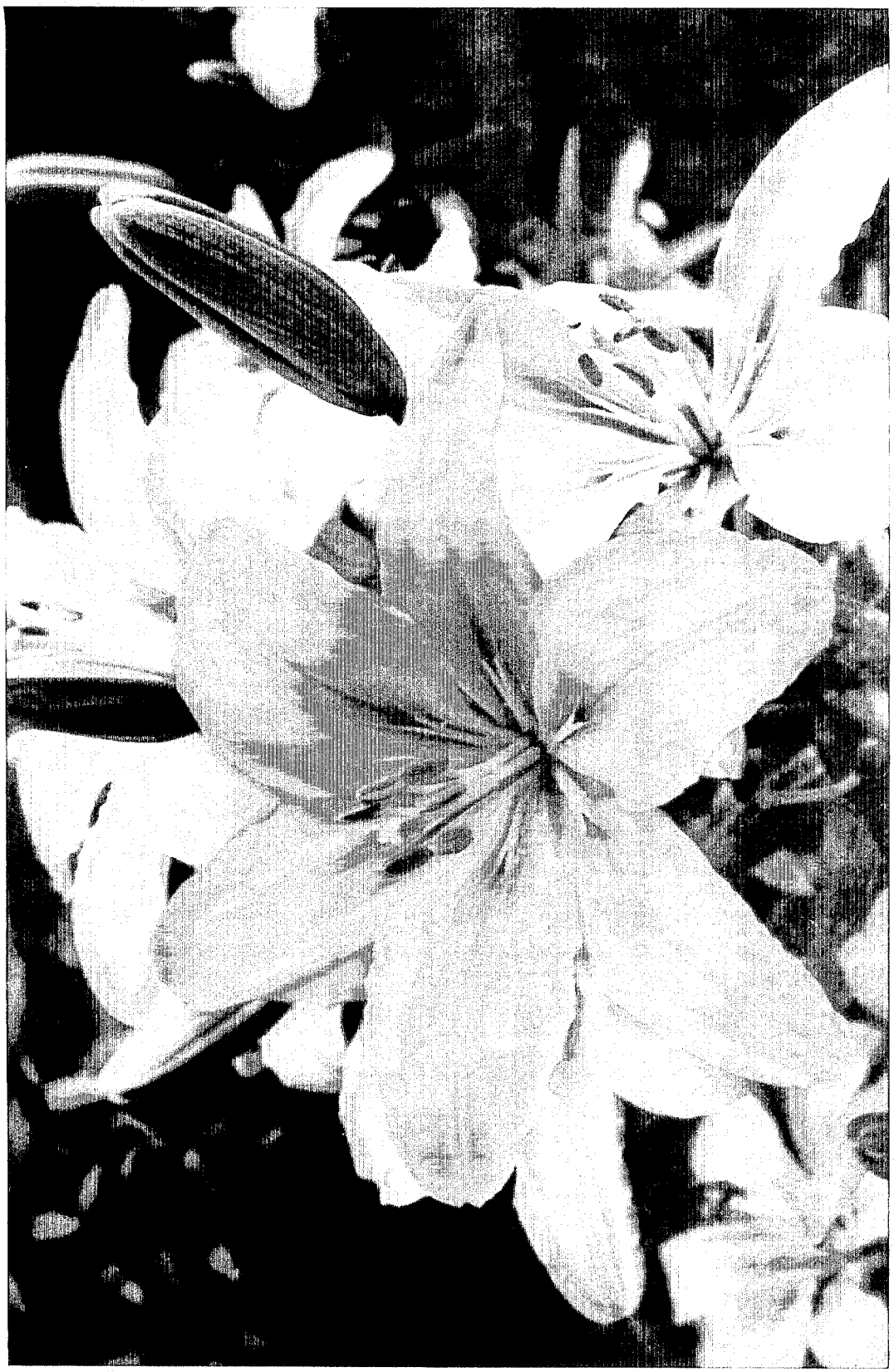

* * * * *